(12) United States Patent
Guillou et al.

(10) Patent No.: US 6,242,396 B1
(45) Date of Patent: Jun. 5, 2001

(54) COSMETIC COMPOSITION FOR REMOVING MAKE-UP FROM AND/OR FOR CLEANSING THE SKIN, IN THE FORM OF A WATER-IN-OIL EMULSION

(75) Inventors: Veronique Guillou, Antony; Isabelle Carton, Paris, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/604,828

(22) Filed: Jun. 28, 2000

(30) Foreign Application Priority Data

Jun. 28, 1999 (FR) .................................. 99 08244

(51) Int. Cl.$^7$ .............................. A61K 7/02; C11D 3/38; C11D 7/50
(52) U.S. Cl. ........................... 510/136; 510/130; 510/466
(58) Field of Search .................................. 510/137, 138, 510/136, 130, 466; 424/78.03

(56) References Cited

U.S. PATENT DOCUMENTS

| | | | | |
|---|---|---|---|---|
| 4,323,468 | * | 4/1982 | Grollier et al. | 252/174.17 |
| 4,880,621 | * | 11/1989 | Grollier et al. | 424/74 |
| 4,960,764 | * | 10/1990 | Figueroa et al. | 514/63 |
| 5,215,749 | * | 6/1993 | Nicoll | 424/401 |
| 5,637,291 | * | 6/1997 | Bara et al. | 424/59 |
| 5,656,280 | * | 8/1997 | Herb et al. | 424/401 |
| 5,871,756 | | 2/1999 | Jeffcoat et al. | 424/401 |

FOREIGN PATENT DOCUMENTS

| | | | |
|---|---|---|---|
| 0456458 | * | 11/1991 | (EP) . |
| 0 463 496 | | 1/1992 | (EP) . |
| 2 136 442 | | 9/1984 | (GB) . |

OTHER PUBLICATIONS

Database Chemical Abstracts; XP–002134148; AN 130:342757.

* cited by examiner

Primary Examiner—Yogendra Gupta
Assistant Examiner—John M. Petruncio
(74) Attorney, Agent, or Firm—Oblon, Spivak, McClelland, Maier & Neustadt, P.C.

(57) ABSTRACT

A cleansing and/or make-up-removing composition, comprising:

in a physiologically acceptable medium, an aqueous phase dispersed in an oily phase with the aid of a silicone emulsifier, wherein the medium comprises (1) at least 78% of aqueous phase, (2) at least one make-up-removing oil selected from the group consisting of fatty acid esters containing at least 12 carbon atoms, and (3), as an emulsifier, the dimethicone copolyol of formula (I)

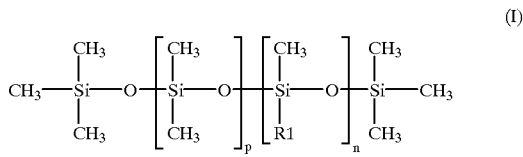

In which $R^1$ represent $-(C_3H_6O)-(C_2H_4O)_{18}-(C_3H_6O)_{18}H$, p=394 and n=4, and wherein the medium is free of branched-chain hydrocarbon-based oil.

13 Claims, No Drawings

COSMETIC COMPOSITION FOR REMOVING MAKE-UP FROM AND/OR FOR CLEANSING THE SKIN, IN THE FORM OF A WATER-IN-OIL EMULSION

BACKGROUND OF THE INVENTION

1. Field of the Invention

The present invention relates to a make-up-removing composition and/or cleansing composition in the form of a water-in-oil emulsion comprising a high water content, at least one make-up-removing oil and a specific silicone surfactant. This composition has the appearance of a cream and is used in particular for removing make-up from and/or for cleansing the skin, the lips and/or the eyes.

2. Description of the Background

The make-up-removing agents and cleansing agents for the face in the form of emulsions, which have conventionally been used to date, have drawbacks that differ according to the sense of the emulsion. In the case of oil-in-water (O/W) emulsions, the external aqueous phase provides freshness. On the other hand, since the oily phase is the internal phase, it is not directly available to dissolve the fatty substances and, as a result, the make-up removal is less effective.

In the case of water-in-oil emulsions, which are very effective at make-up removal/cleansing because of the fact that the fatty phase is directly available to dissolve the various fatty substances present on the skin or derived from the make-up, they are uncomfortable to use because of the greasy, heavy sensation afforded by this external fatty phase which remains on the skin.

In cleansing the face, women are looking for a "sensation of water", water being the symbol of cleanliness and purity, which are values that are greatly associated with cleansing, while at the same time retaining high make-up-removing and/or cleansing efficacy. Cleansing or make-up-removing products using water are derived from an entirely different technology, namely foaming bars, creams or gels. For certain types of skin, in particular dry and sensitive skin, these products lead to tautness, drying of the skin or even intolerance reactions.

Thus, there is a need for an effective cleansing and/or make-up-removing composition which provides a sensation of freshness without having the drawbacks known in the prior art.

SUMMARY OF THE INVENTION

Accordingly, one object of the present invention is to provide a skin cleansing and/or make-up removing composition which is effective and leaves a sensation of freshness to the skin without a feeling of tautness or an intolerance reaction.

Briefly, this object and other objects of the present invention as hereinafter will become more readily apparent can be attained by a cleansing and/or make-up-removing composition comprising, in a physiologically acceptable medium, an aqueous phase dispersed in an oily phase with the aid of a silicone emulsifier, wherein the medium comprises (1) at least 78% of aqueous phase, (2) at least one make-up-removing oil selected from the group consisting of fatty acid esters containing at least 12 carbon atoms, and (3), as an emulsifier, the dimethicone copolyol of formula (I):

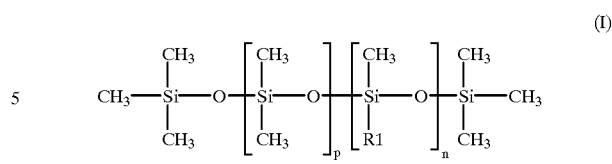

In which $R^1$ represents —$(C_3H_6O)$—$(C_2H_4O)_{18}$—$(C_3H_6O)_{18}H$, p=394 and n=4, and wherein the medium is free of branched-chain hydrocarbon-based oil.

DETAILED DESCRIPTION OF THE PREFERRED EMBODIMENTS

The expression "physiologically acceptable medium" means a medium which is compatible with the skin, the lips, the eyes, the scalp and/or the hair.

The expression "free of branched-chain hydrocarbon-based oil" refers to the fact that in which $R^1$ represents —$(C_3H_6O)$—$(C_2H_4O)_{18}$—$(C_3H_6O)_{18}H$, p=394 and n=4, and wherein the for example, isoparaffins, isohexadecane and isododecane.

Despite the large amount of aqueous phase in the composition, the composition of the invention is stable over time. In addition, it has a specific Theological characteristic which makes it particularly advantageous to use in the fields under consideration. The reason for this is that, when it is applied to the skin and after massaging for a few moments, which is essential to dissolve the fatty substances to be removed, the emulsion "breaks", i.e. it suddenly becomes fluid, thus releasing the aqueous phase and generating a great sensation of freshness.

The composition of the invention preferably has a viscosity ranging from 3 Pa·s (30 poises) to 20 Pa·s (200 poises). This viscosity is measured using a Rheomat 180 machine, i.e. the Rheomat RM180 machine from the company Mettler.

The composition of the invention comprises at least 78% by weight of aqueous phase relative to the total weight of the composition and preferably at least 80% of the total weight of the composition. The aqueous phase can constitute up to 92% of the total weight of the composition. The aqueous phase comprises water and optionally water-soluble compounds such as, in particular, alcohols and polyols.

The water preferably constitutes at least 65%, more preferably at least 70% of the total weight of the composition.

Moreover, in a preferred embodiment of the invention, the aqueous phase contains, as water-soluble compounds, one or more lower alcohols or polyols. The expression "lower alcohol" refers to alcohols containing from 1 to 6 and more particularly from 1 to 4 carbon atoms, such as ethanol. Polyols which may be mentioned, for example, include glycerol, propylene glycol and polyethylene glycols (for example PEG-8). These alcohols and/or polyols may be present in the composition in an amount preferably ranging from 0.5 to 25% more preferably from 1 to 15% of the total weight of the composition.

Moreover, the composition of the invention contains, as an emulsifier, and preferably as sole emulsifier, the dimethicone copolyol of formula (I). This dimethicone copolyol can be in the form of a mixture with a volatile or non-volatile silicone oil, and in particular with cyclomethicones (D4 or D5) and/or polydimethylsiloxanes of different viscosities and in particular 5 cst and 10 cst.

The dimethicone copolyol containing mixtures below marketed by the company Dow Corning are particularly preferred for use in the composition of the invention:

a mixture of the compound of formula (I), tetracyclomethicone (D4) and water (weight ratio 10/88/2), sold under the name DC 3225C;

a mixture of the compound of formula (I), pentacyclomethicone (D5) and water (weight ratio 10/88/2), sold under the name DC 5225C;

a mixture of the compound of formula (I) and polydimethylsiloxane 5 cst (weight ratio 10/90), sold under the name DC 3225C in 200 Fluid 5 cst;

a mixture of the compound of formula (I) and polydimethylsiloxane 10 cst (weight ratio 10/90), sold under the name DC 3225C in 200 Fluid 10 cst; and a mixture of the compound of formula (I) and pentacyclomethicone (D5) (weight ratio 43/57), sold under the name DC 51 85C.

The emulsifier of formula (I) is preferably present in an amount of active material ranging from 0.1 to 5%, more preferably from 0.5 to 3% by weight relative to the total weight of the composition.

Even when the composition is free of any other emulsifier, the composition remains stable over time.

Preferably, the oily phase/emulsifier weight ratio is greater than or equal to 5, more preferably greater than or equal to 8.

The oily phase of the composition of the invention contains at least one make-up-removing oil selected from the group consisting of fatty acid esters containing at least 12 carbon atoms.

The make-up-removing oil is selected from the group consisting of fatty acid esters containing at least 12 carbon atoms. These esters are preferably obtained from a straight-chain or branched-chain alcohol containing from 1 to 17 carbon atoms and from a straight-chain or branched-chain fatty acid containing at least 12 carbon atoms and preferably from 14 to 22 carbon atoms. They are preferably mono- or diesters.

Preferably, the make-up-removing oil is selected from the group consisting of the group of esters which comprise no unsaturation and/or no ether or hydroxyl groups. Even more advantageously, the make-up-removing oil is a saturated ester which contains no ether or hydroxyl groups.

Thus, the make-up-removing oil in the composition of the invention can be selected, in particular, from the group consisting of 2-ethylhexyl palmitate (or octyl palmitate), 2-ethylhexyl myristate (or octyl myristate), isopropyl palmitate, isopropyl myristate, diisopropyl adipate, dioctyl adipate, 2-ethylhexyl hexanoate, ethyl laurate, methyl myristate, octyl dodecyl octanoate, isodecyl neopentanoate, ethyl myristate, myristyl propionate, 2-ethylhexyl 2-ethylhexanoate, 2-ethylhexyl octanoate, 2-ethylhexyl caprate/caprylate, methyl palmitate, butyl myristate, isobutyl myristate, ethyl palmitate, isohexyl laurate, hexyl laurate and isopropyl isostearate, and mixtures thereof.

The amount of make-up-removing oil(s) can constitute all or a portion of the oily phase, and for example from 1 to 90%, more preferably from 5 to 70% of the total weight of the oily phase.

The oily phase can also contain any fatty substance and in particular non-make-up-removing oils other than those mentioned above, conventionally used in the cosmetics field. As other oils which may be present in the oily phase mention may be made, for example, of mineral oils containing a linear hydrocarbon-based chain, such as liquid petroleum jelly, oils of plant origin such as apricot kernel oil; synthetic oils; volatile or non-volatile silicone oils and fluoro oils. The other fatty substances which may be present in the oily phase may be, for example, fatty acids, fatty alcohols and waxes.

The oily phase is present in the composition of the invention in an amount ranging from 1 to 21.5% and preferably from 3 to 18% by weight relative to the total weight of the composition.

In a known manner, the composition of the invention can also contain adjuvants that are common in the cosmetics field, such as hydrophilic or lipophilic active agents, preserving agents, antioxidants, fragrances, solvents, fillers, sunscreens, dyestuffs (pigments or dyes), basic agents (triethanolamine), acidic agents or lipid vesicles. These adjuvants are used in the proportions that are usual in cosmetics or dermatology, and for example from 0.01 to 30% relative to the total weight of the composition, and they are introduced, depending on their nature, into the aqueous phase or into the oily phase of the emulsion, or into vesicles. These adjuvants and their concentrations should be such that they do not modify the property which is desired for the composition.

An aspect of the present invention is also a cosmetic process for removing make-up from and/or for cleansing the skin, the lips and/or the eyes, characterized in that a composition as defined above is applied to the skin, the lips and/or the eyes.

Still another aspect of the invention is the cosmetic use of the composition as defined above to remove make-up from and/or to cleanse the skin, the lips and/or the eyes.

Having now generally described this invention, a further understanding can be obtained by reference to certain specific Examples which are provided herein for purposes of illustration only and are not intended to be limiting unless otherwise specified. The amounts given below are given as percentages by weight, except where otherwise mentioned.

EXAMPLE

Example: Emulsion for Removing Make-up from the Face

| A. Oily phase | | |
|---|---|---|
| Dimethicone copolyol of formula (I) in pentacyclomethicone and water (10/88/2) (DC 5225 C) | | 9.2% |
| Liquid petroleum jelly | | 3.2% |
| Isopropyl palmitate | | 3% |
| B. Aqueous phase | | |
| Sodium chloride | | 2.5% |
| Glycerol | | 5% |
| Ethanol | | 5% |
| Preserving agents | | 0.65% |
| Sodium salt of EDTA | | 0.1% |
| PEG-8 | | 4% |
| Water | qs | 100% |

Procedure: Phase A is prepared by mixing the constituents together with stirring at 600 rpm. Phase B is prepared separately and a portion (about 1/10) of phase B is introduced into phase A very slowly with stirring. The rest of phase B is they added more quickly, still with stirring, and stirring is continued for a certain period of time.

A white cream is obtained which has a viscosity, as measured using a Rheomat 180 machine with spindle 4, of 5.74 Pa·s (57.4 poises) at time zero. This viscosity stabilizes after 10 minutes at 4.56 Pa·s (45.6 poises).

During the removal of make-up or cleansing, the composition is massaged on the skin for a few seconds (5 to 10 seconds). At the end of this time, it "breaks", affording a great sensation of freshness while at the same time removing make-up from or cleansing the skin perfectly. The cream is then wiped off with a pad of cotton wool or a tissue.

The disclosure of French priority Application Number 9908244 filed Jun. 28, 1999 is hereby incorporated by reference into the present application.

Obviously, numerous modifications and variations of the present invention are possible in light of the above teachings. It is, therefore, to be understood that within the scope of the appended claims, the invention may be practiced otherwise than as specifically described herein.

What is claimed as new and is intended to be secured by Letters Patent is:

1. A cleansing and/or make-up removing water-in-oil emulsion composition, comprising:

a physiologically acceptable medium which is an aqueous phase dispersed in an oily phase with the aid of a silicone emulsifier, wherein the medium comprises (1) at least 78% of aqueous phase, (2) at least one make-up-removing oil selected from the group consisting of fatty acid esters containing at least 12 carbon atoms, and (3), an emulsifier comprising the dimethicone copolyol of formula

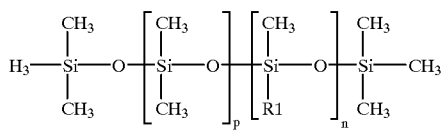
(I)

in which $R^1$ represents $-(C_3H_6O)-(C_2H_4O)_{18}-(C_3H_6O)_{18}H$, p=394 and n=4, and wherein the medium is free of branched-chain hydrocarbon-based oil.

2. The composition according to claim 1, wherein the emulsifier is in a mixture with at least one silicone oil.

3. The composition according to claim 1, wherein the emulsifier is present in an amount ranging from 0.5 to 5% by weight relative to the total weight of the composition.

4. The composition according to claim 1, wherein the oily phase is present in an amount ranging from 1 to 21.5% by weight relative to the total weight of the composition.

5. The composition according to claim 1, wherein the oily phase/emulsifier weight ratio is greater than or equal to 5:1.

6. The composition according to claim 5, wherein the oily phase/emulsifier weight ratio is greater than or equal to 8:1.

7. The composition according to claim 1, wherein the make-up removing oil is selected from the group consisting of esters obtained from a straight-chain or branched-chain alcohol containing from 1 to 17 carbon atoms and from a straight-chain or branched-chain fatty acid containing from 14 to 22 carbon atoms.

8. The composition according to claim 7, wherein the make-up-removing oil is selected from the group consisting of 2-ethylhexyl palmitate, 2-ethylhexyl myristate, isopropyl palmitate, isopropyl myristate, diisopropyl adipate, dioctyl adipate, 2-ethylhexyl hexanoate, ethyl laurate, methyl myristate, octyldodecyl octanoate, isodecyl neopentanoate, ethyl myristate, myristyl propionate, 2-ethylhexyl 2-ethylhexanoate, 2-ethylhexyl octanoate, 2-ethylhexyl caprate/caprylate, methyl palmitate, butyl myristate, isobutyl myristate, ethyl palmitate, isohexyl laurate, hexyl laurate, isopropyl isostearate and mixtures thereof.

9. The composition according to claim 1, wherein the aqueous phase contains at least one lower alcohol and/or one polyol.

10. The composition according to claim 9, wherein the amount of lower alcohol and/or of polyol ranges from 0.5 to 25% by weight relative to the total weight of the composition.

11. The composition according to claim 10, wherein the amount of lower alcohol and/or of polyol ranges from 1 to 15% by weight relative to the total weight of the composition.

12. A cosmetic process, comprising:

applying the composition according to claim 1 to the skin in order to remove make-up from and/or for cleansing the skin, the lips and/or the eyes.

13. A water-in-oil emulsion for removing make-up from the face as defined in claim 1 consisting of

| | | |
|---|---|---|
| A) | A continuous oily phase composed of | |
| | Dimethicone copolyol of formula (I) in pentacyclomethicone and water (10/88/2) | 9.2% |
| | Liquid petroleum jelly | 3.2% |
| | Isopropyl palmitate | 3% |
| and | | |
| B) | A dispersed aqueous phase composed of | |
| | Sodium chloride | 2.5% |
| | Glycerol | 5% |
| | Ethanol | 5% |
| | Preserving agents | 0.65% |
| | PEG-8 | 4% |
| | Water | qs 100% . |

* * * * *